(12) United States Patent
Truckai et al.

(10) Patent No.: US 11,737,911 B2
(45) Date of Patent: *Aug. 29, 2023

(54) SYSTEMS AND METHODS FOR PERMANENT FEMALE CONTRACEPTION

(71) Applicant: Meditrina, Inc., San Jose, CA (US)

(72) Inventors: Csaba Truckai, Saratoga, CA (US); John H. Shadduck, Menlo Park, CA (US)

(73) Assignee: Meditrina, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/304,297

(22) Filed: Jun. 17, 2021

(65) Prior Publication Data

US 2021/0353452 A1    Nov. 18, 2021

Related U.S. Application Data

(63) Continuation of application No. 14/951,263, filed on Nov. 24, 2015, now Pat. No. 11,065,146.

(60) Provisional application No. 62/083,838, filed on Nov. 24, 2014.

(51) Int. Cl.
| | |
|---|---|
| *A61F 6/22* | (2006.01) |
| *A61F 6/20* | (2006.01) |
| *A61B 18/14* | (2006.01) |
| *A61M 1/00* | (2006.01) |
| *A61B 18/20* | (2006.01) |
| *A61M 25/09* | (2006.01) |
| *A61B 18/00* | (2006.01) |
| *A61B 17/42* | (2006.01) |
| *A61B 18/02* | (2006.01) |

(52) U.S. Cl.
CPC .......... *A61F 6/225* (2013.01); *A61B 18/1492* (2013.01); *A61B 18/20* (2013.01); *A61F 6/208* (2013.01); *A61M 1/84* (2021.05); *A61M 25/09* (2013.01); *A61B 2017/4233* (2013.01); *A61B 2018/0063* (2013.01); *A61B 2018/00214* (2013.01); *A61B 2018/00559* (2013.01); *A61B 2018/00577* (2013.01); *A61B 2018/00994* (2013.01); *A61B 2018/0212* (2013.01); *A61B 2018/1467* (2013.01); *A61B 2218/007* (2013.01)

(58) Field of Classification Search
CPC .... A61F 6/225; A61F 6/22; A61F 6/20; A61F 6/00; A61F 6/202; A61F 6/204; A61F 6/206; A61F 6/208; A61B 2018/00559; A61B 2018/00577; A61B 2018/00583; A61B 2017/4233; A61B 17/12; A61B 2018/0063; A61B 17/42; A61B 17/12031
See application file for complete search history.

(56) References Cited

U.S. PATENT DOCUMENTS

| | | |
|---|---|---|
| 4,700,701 A | 10/1987 | Montaldi |
| 5,122,137 A | 6/1992 | Lennox |
| 5,303,719 A | 4/1994 | Wilk et al. |
| 5,891,141 A | 4/1999 | Rydell |
| 6,042,590 A | 3/2000 | Sporri et al. |

(Continued)

FOREIGN PATENT DOCUMENTS

WO    WO 2016/086051    6/2016

*Primary Examiner* — Victoria Hicks Fisher
(74) *Attorney, Agent, or Firm* — Levine Bagade Han LLP

(57) ABSTRACT

Methods and devices for treating and occluding a female patient's fallopian tubes to provide permanent or extended birth control or sterilization.

7 Claims, 13 Drawing Sheets

(56) References Cited

U.S. PATENT DOCUMENTS

| | | | |
|---|---|---|---|
| 6,378,524 B1 | 4/2002 | Jones | |
| 6,595,989 B1 | 7/2003 | Schaer | |
| 7,846,160 B2 | 12/2010 | Payne et al. | |
| 7,905,880 B2 | 3/2011 | Harrington et al. | |
| 8,613,282 B2 | 12/2013 | Nikolchev et al. | |
| 11,065,146 B2 * | 7/2021 | Truckai | A61B 18/20 |
| 2005/0232961 A1 | 10/2005 | Lowe et al. | |
| 2006/0009798 A1 | 1/2006 | Callister et al. | |
| 2007/0265613 A1 | 11/2007 | Edelstein et al. | |
| 2010/0006105 A1 | 1/2010 | Carter et al. | |
| 2011/0087109 A1 | 4/2011 | Swann | |
| 2013/0139827 A1 | 6/2013 | Nikolchev et al. | |
| 2016/0270950 A1 | 9/2016 | Truckai et al. | |

* cited by examiner

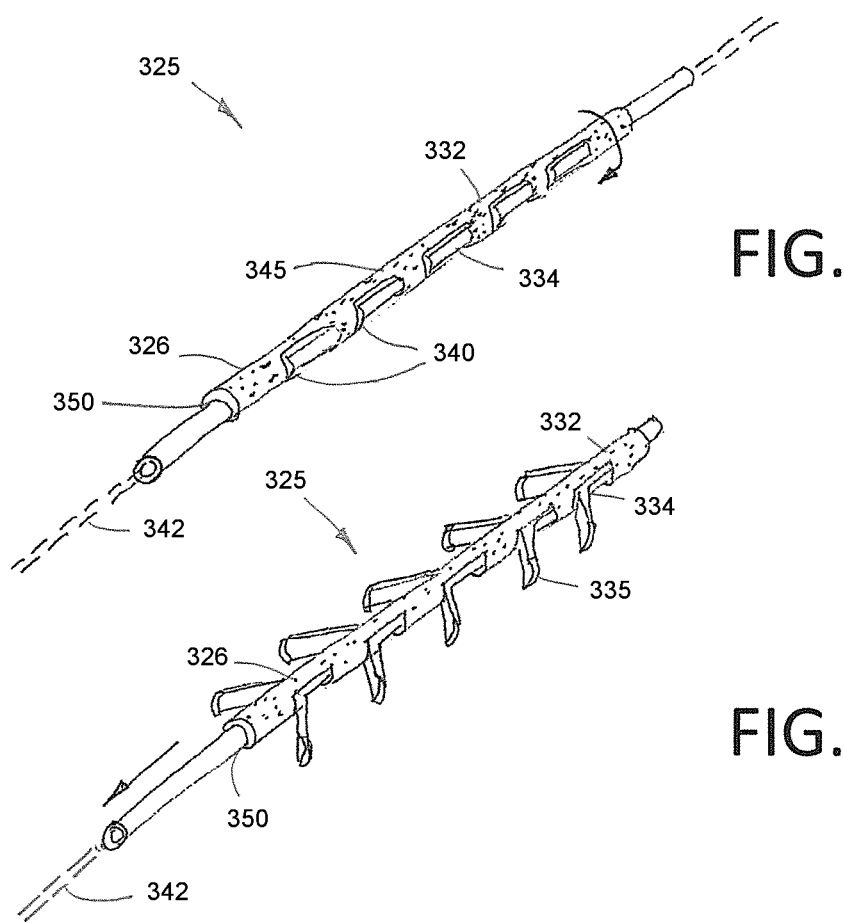

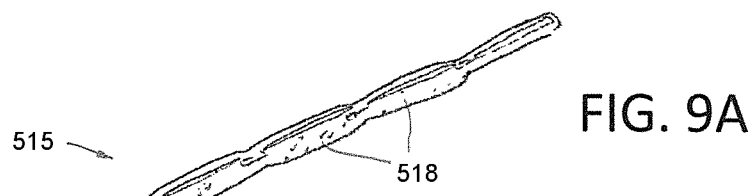
FIG. 9A
FIG. 9B
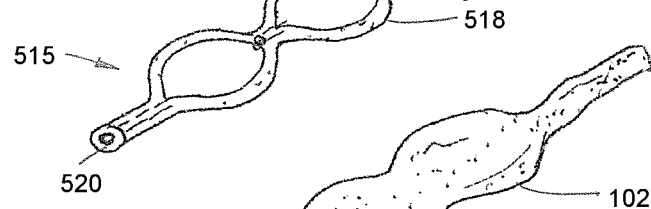
FIG. 9C
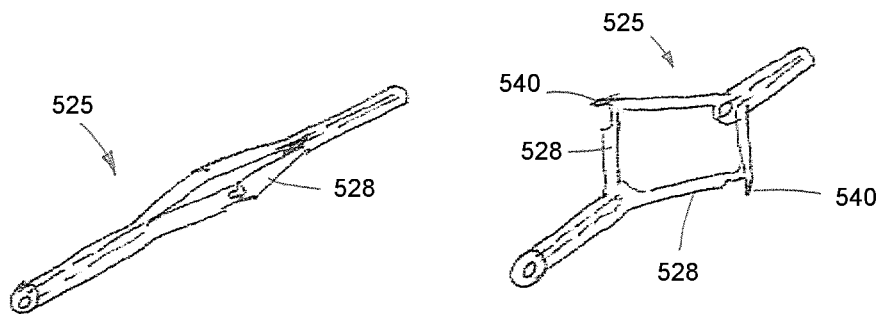
FIG. 10A
FIG. 10B

SYSTEMS AND METHODS FOR PERMANENT FEMALE CONTRACEPTION

CROSS-REFERENCE TO RELATED APPLICATIONS

This application is a continuation of U.S. application Ser. No. 14/951,263, filed Nov. 24, 2015, now U.S. Pat. No. 11,065,146, which claims benefit of priority to U.S. Provisional Application No. 62/083,838, filed Nov. 24, 2014, the contents of each of which is incorporated by reference herein in its entirety.

FIELD OF THE INVENTION

The present invention relates to medical devices and methods for treating and occluding a female patient's fallopian tubes to provide permanent birth control or sterilization.

BACKGROUND

Female sterilization typically involves occluding a patient's fallopian tubes, with various procedures using laparoscopic or minimally invasive trans-cervical approaches. One procedure involves placing flexible coil-like devices into the fallopian tubes, which are made of polyester fibers and metal wires. Tissue in-growth into the implanted devices can block the fallopian tubes. However, such implants are worrisome due to potential unknown long-term effects.

SUMMARY OF THE INVENTION

The present invention is directed to catheter systems and implants together with methods of using such systems and devices device for occluding reproductive body lumens such as a female's fallopian tubes.

The tubal occlusion procedure described herein is a minimally invasive procedure in which a device can be introduced into the patient's uterine cavity trans-cervically. In one aspect of the method of the invention, RF energy is used to ablate a thin layer of tissue in a segment of a fallopian tube which can be performed very rapidly, for example in 5 to 60 seconds. A second step of the method involves cutting or damaging tissue within the segment to cause trauma, including but not limited to irritation, bleeding, burning, separation, etc., where such trauma leads to a subsequent adhesion formation across the area of injury. The wound healing response and adhesion of the walls in the segment can permanently close the fallopian tube.

The details of one or more embodiments of the invention are set forth in the accompanying drawings and the description below. Other features, objects, and advantages of the invention will be apparent from the description and drawings, and from the claims.

In one variation, the device includes a system and/or device for occluding a fallopian tube. Such devices or systems can be coupled to a power supply, vacuum source, etc. to perform the acts described herein.

In one example, such a device comprises a device body having a lumen passing therethrough, the device body being moveable between a first profile and a second profile where in the second profile the device body increases in a planar dimension such that than when located inside the fallopian tube the device body flattens the fallopian tube; at least one adhesion producing surface coupled to the device body and configured to create trauma to a wall of the fallopian tube to produce a wound healing response; at least one energy delivery surface on or in the device body and configured to transmit energy from an energy delivery source to the wall of the fallopian tube.

In another variation of the device the second profile comprises a non-linear shape and where the device body is maintained in tension to assume the first profile.

The adhesion producing surface comprises a cutting element. Variations include that the cutting element is advanceable through the lumen and through an opening in the device body.

The device can also be coupled to a vacuum source that is fluidly engaged with a vacuum lumen extending through the device body, where the vacuum lumen is in fluid communication with at least one vacuum port located in the device body, where the vacuum lumen is fluidly coupleable to a vacuum source.

The devices described herein can be advanced with a catheter and/or a guidewire, or a combination thereof. When used with a guidewire, the guidewire can extend through the lumen of the device body.

In certain variations, the device includes at least one energy delivery opening on the device body and where at least one of the energy delivery surfaces is located on the guidewire such that the energy delivery opening permits contact of the guidewire with the wall of the fallopian tube.

The adhesion producing surface can be located on an edge of the device body when in the second profile, and where rotation of the device body causes the adhesion producing surface to create trauma to the wall of the fallopian tube.

The device can include at least one hinged element located on the device body, where movement of the hinged element away from the device body causes the device body to assume the second profile. In certain variations, the adhesion producing surfaces is on the at least one hinged element.

Variations of the device can include at least one leg member being extendable from the device body, such that when extended, the device body assumes the second profile.

The devices described herein can be configured such that the device body can be elastically moveable between the first profile and the second profile or plastically deformable between the first profile and the second profile.

Variations of the device can include a device body comprising a flexible polymer and where the at least one adhesion surface comprises an abrasive surface located on the device body.

BRIEF DESCRIPTION OF THE DRAWINGS

FIG. 1A illustrates an initial step in a method wherein a hysteroscope is introduced trans-cervically into the uterine cavity and the catheter is advanced toward the opening of a fallopian tube.

FIG. 7A is a perspective view of another variation of occluding device or implant in a collapsed or non-extended position.

FIG. 7B is a view of the implant of FIG. 7A in an extended position.

FIG. 9A is a perspective view of another variation of occluding device or implant in an insertion configuration.

FIG. 9B is a view of the implant of FIG. 9A is a deployed configuration.

FIG. 9C is a view of the implant of FIG. 9B deployed in a fallopian tube to thereby flatten the tube.

FIG. 10A is a perspective view of another variation of occluding device or implant in an insertion configuration.

FIG. 10B is a view of the implant of FIG. 10A is a deployed configuration.

DETAILED DESCRIPTION THE INVENTION

Figure 1A:
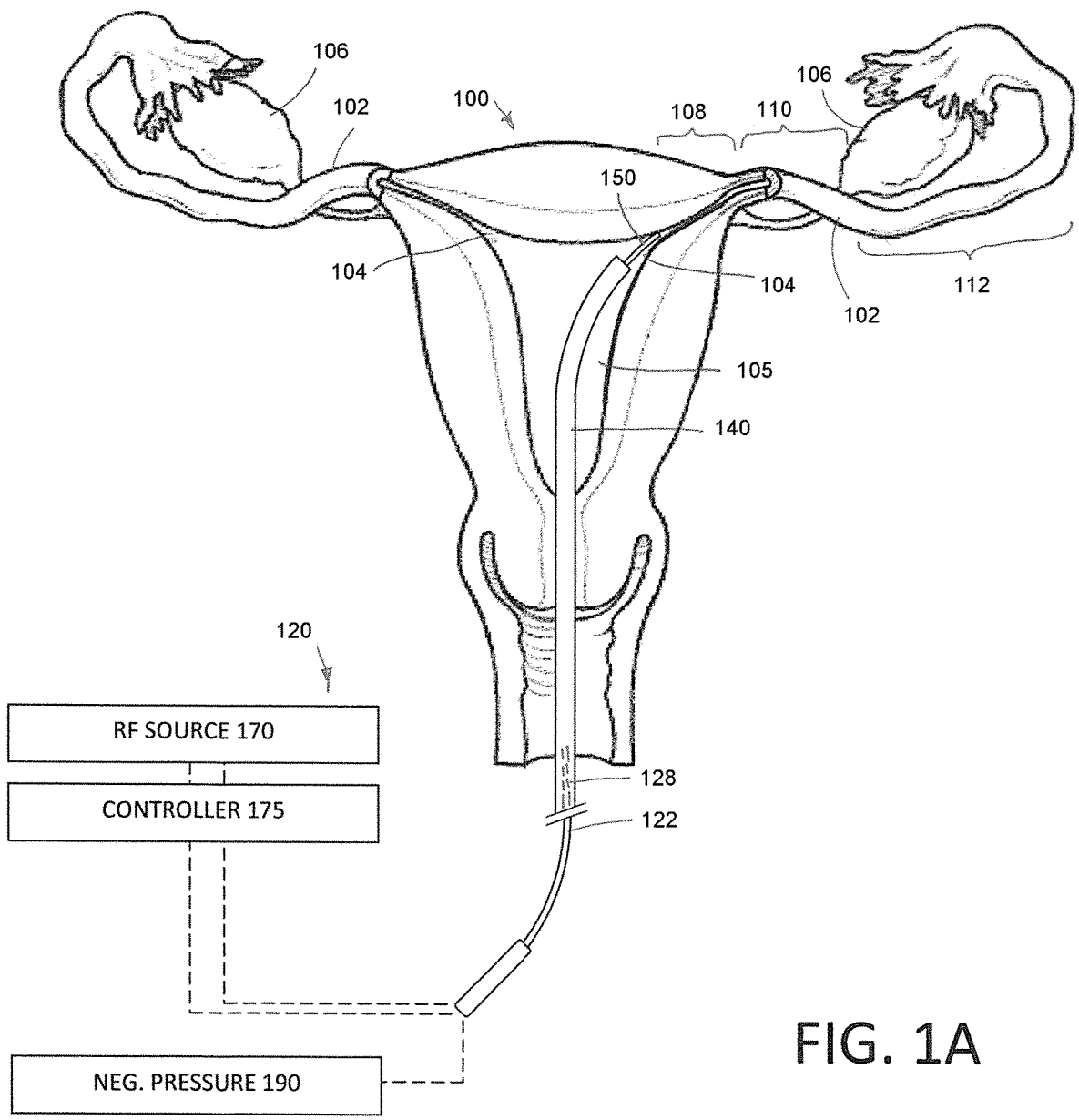
FIG. 1A is a sectional view of a patient's uterus and fallopian tubes showing a variation of a system for occluding a fallopian tube, wherein the system includes a catheter carrying an implant.
Figure 1B:
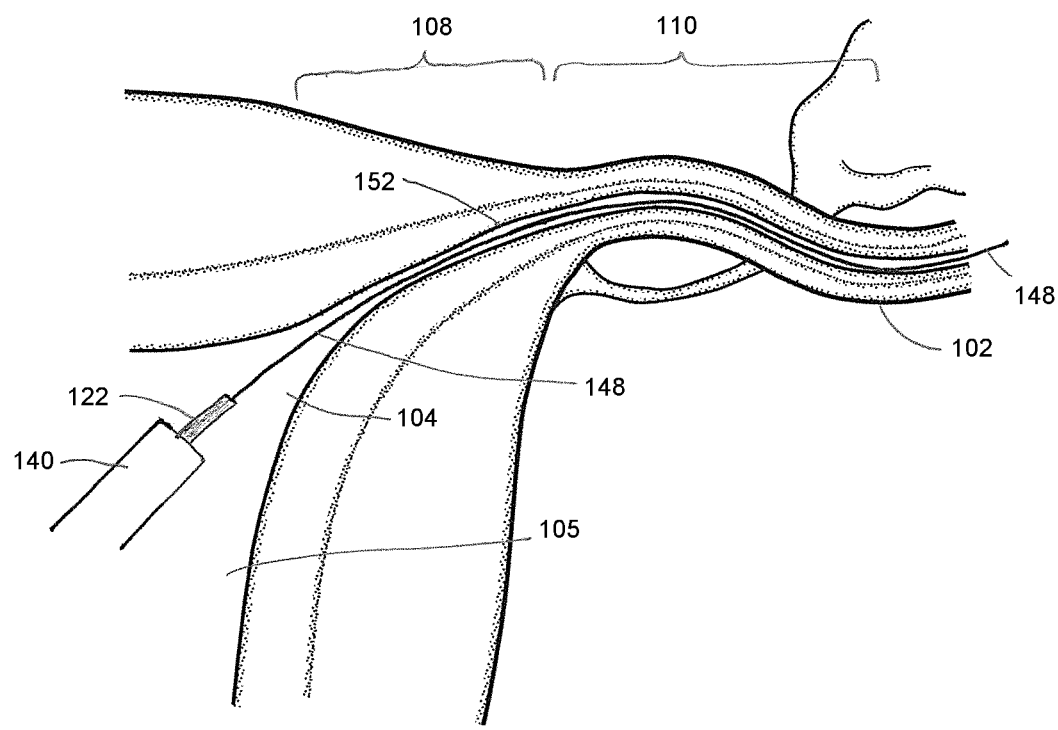
FIG. 1B is an enlarged view of a portion of the uterus and fallopian tube of FIG. 1A illustrating another step in a method of the invention wherein a guidewire is advanced through the catheter and into the fallopian tube.

FIG. 1A illustrates a patient's uterus 100 and fallopian tubes 102 or oviducts, which are paired, tubular conduits that extend from the cornua 104 of the uterine cavity 105 us toward the ovaries 106. Each fallopian is about 7 cm to 14 cm in length and is defined by three different sections: the intramural segment 108, the isthmus segment 110 and the ampulla 112 (FIGS. 1A-1B). The intramural or interstitial segment 108 of the tube continues from the cornua 104 to the isthmus 110 and is about 1 cm in length with a 1 mm lumen diameter. The isthmus 108 is a round cord-like structure that constitutes the medial one-third of the fallopian tube with a 2 mm to 10 mm outer diameter. The lumen of the fallopian tube is lined with a layer of mucous membrane that can have many folds and papillae. The wall of the fallopian tube includes layers of muscle tissue. The innermost layer has spirally arranged fibers, the middle layer has circular fibers, and an outer layer has longitudinal muscle fibers. These muscle fibers provide for peristalsis and antiperistalsis in the fallopian tubes.

FIGS. 1A-1E and 2A-2B illustrate a system 120 that includes an elongate catheter 122 that carries a releasable occluding device or implant 125 (FIG. 2A) adapted to occlude a patient's reproductive lumen such as fallopian tube 102. The catheter 122 can have any suitable length for extending through the working channel 128 of a hysteroscope or endoscope 140. In one embodiment shown in FIGS. 1A-1D, the hysteroscope 140 is an articulating scope that can be articulated in the uterine cavity 105 to view the entry to the fallopian tubes 102 and direct the catheter into a fallopian tube 102. In another variation, a straight rigid endoscope could be used with an appropriate viewing angle of 5° to 30° together with a catheter or catheter sleeve that can be articulated to assist in directing a catheter working end into a fallopian tube.

Figure 2A:
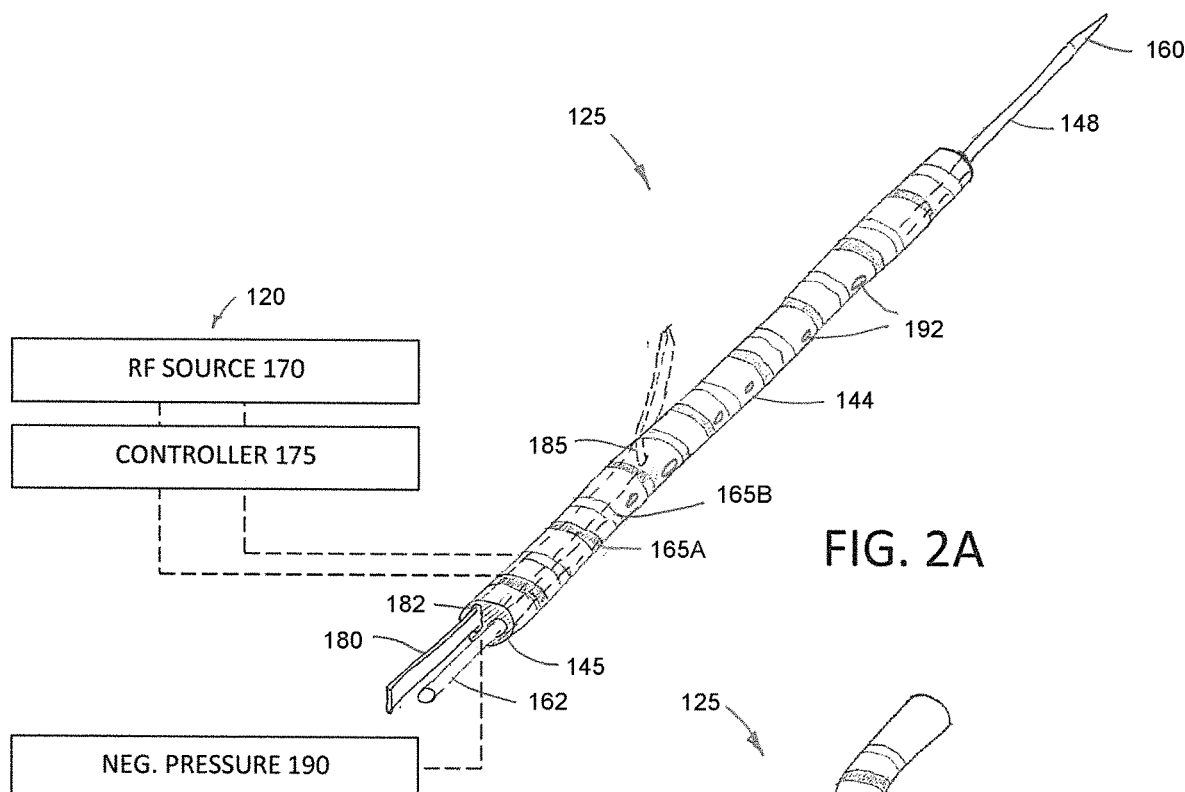
FIG. 2A is an isometric view of an occluding device or implant carries by the catheter of FIGS. 1A-1D, with the implant body being maintained in a tensioned linear shape by the guidewire in a passageway of the implant, with FIG. 2A further illustrating a blade element that can be extended from the implant to cause trauma in the targeted site in the step of FIG. 1D.
Figure 2B:
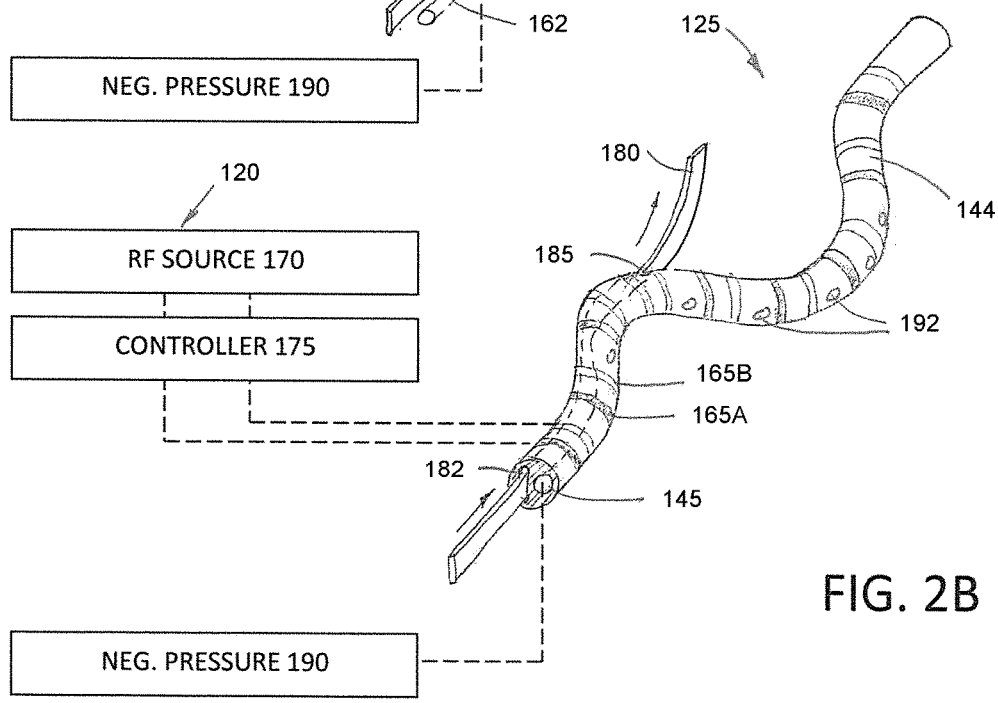
FIG. 2B is another view of the implant of FIG. 2A with the implant body in a non-tensioned shape having multiple curves with the guidewire withdrawn from the implant, and further illustrating the blade element extended from the implant for causing trauma in the targeted site, for example, in the step of FIG. 1E.

In one variation of implant 125 shown in FIGS. 2A-2B, the body 144 of the implant comprises a polymeric material with a passageway 145 to allow it advancement over a guidewire 148. In general, the variations of catheter working end 150 and implant 125 disclosed herein are adapted to provide functionality in more than one aspect which thus enables the system to effectively occlude fallopian tubes to provide permanent contraception. In one aspect and function, the system and/or implant provide a mechanism to deliver energy to the catheter's working end or implant to ablate tissue in the fallopian tube lumen 152 over an elongated segment. As will be described further below, the ablation of endothelial tissue over an elongated segment prevents that rapid re-epithelialization of the lumen, and ablation of underlying muscle layers prevents peristalsis which otherwise could move or disrupt coagulum described next. In a second aspect, the system and/or implant provide means for causing trauma with a targeted segment of a fallopian tube. As will be described further below, bleeding and coagulum at the targeted site will optimize conditions for fibrosis and adhesion formation in the targeted site for permanent occlusion. In a third aspect, as will be described further below, the implant 150 provides a 'dam' for preventing displacement of the coagulum following bleeding to allow time for the adhesion to fully develop across to coagulum. In a fourth aspect, as will be described further below, the implant 150 provides a means for approximating fallopian tube walls to lessen or eliminate the adhesion dimension between the walls to accelerate the time required for adhesion formation. In a fifth aspect, as will be described further below, the implant 150 had a very flexible body 144 to allow its insertion into a tortuous path of a fallopian tube over a flexible guidewire. In a sixth aspect, as will be described further below, the implant 125 provides a means for resisting movement of the implant within the fallopian tube 102 which can be the overall shape of the implant or barb-like features on the implant or adhesives carried by the implant for engaging tissue. In a seventh aspect, as will be described further below, the implant 125 can be fabricated at least partly of micro-porous polymeric material that allows for tissue in-growth in a scaffold-like implant body. In an eighth aspect, as will be described further below, the implant 125 can be fabricated at least partly of bio-absorbable or bio-degradable material which will lessen its bulk following absorption or degradation.

FIGS. 1A-1E provide an overview of the steps in a method corresponding to the examples disclosed herein, and further functional details of the system 120 and implant 125 in each of the steps follow this overview.

In FIG. 1A, an articulating hysteroscope 140 is introduced trans-cervically and articulated to view in the direction of a fallopian tube 102. The catheter 122 together with a guidewire 148 is then introduced through the working channel 128 of the hysteroscope.

Figure 1C:
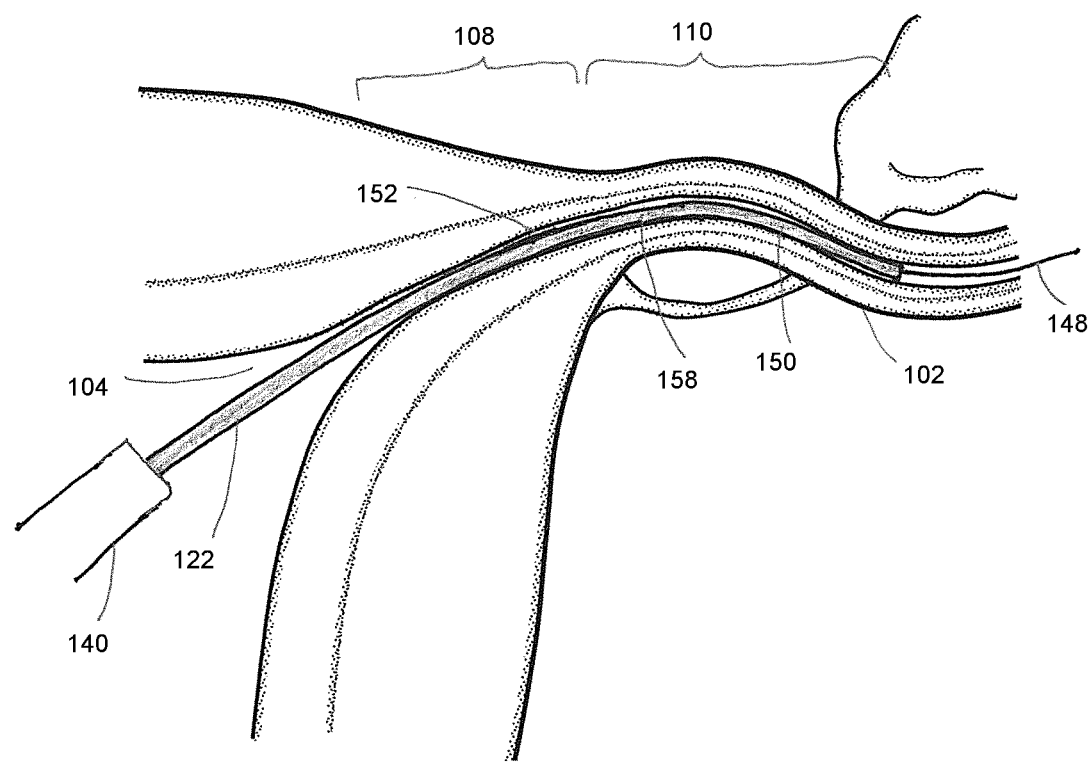
FIG. 1C is a view similar to that of FIG. 1B illustrating another step in the method wherein the catheter and implant are advanced over the guidewire to a targeted site in the fallopian tube.

FIG. 1B illustrates a subsequent step wherein the physician introduces guidewire 148 into and through the lumen of the fallopian tube 102 to at least the isthmus segment 110. FIG. 1C then shows another step in which the catheter working end 150 is advanced over the guidewire 148 into the fallopian tube 102.

FIG. 1C illustrates one embodiment of implant 125 that is carried by the catheter working end within a thin-wall sheath 158 that can be retracted to expose the implant 125.

Figure 1D:
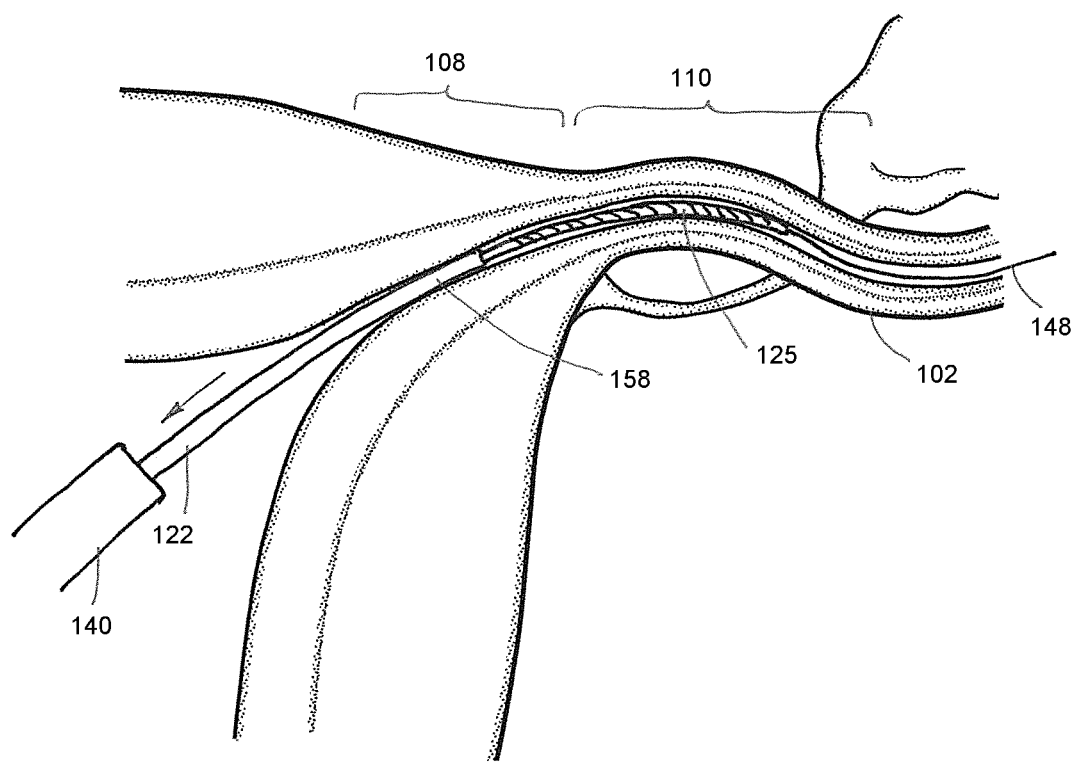
FIG. 1D is a view similar to that of FIG. 1C illustrating another step in the method wherein a retaining sleeve carried by the catheter is retracted to expose the implant in the targeted site in the fallopian tube, and FIG. 1C also illustrates a subsequent step of delivering ablative energy to walls of the fallopian, and another step of causing trauma in the site as further shown in FIG. 2A.

FIG. 1D next shows another step in which the sheath 158 is retracted to expose and deploy the implant 125 in the intramural and or isthmus segment of the fallopian tube 102. At this step, the system and implant can be actuated to cause trauma in the targeted segment of the fallopian tube. Also at this step, the implant 125 is still operatively coupled to the catheter to allow energy delivery from a remote energy source to the implant as will be described below.

Figure 1E:
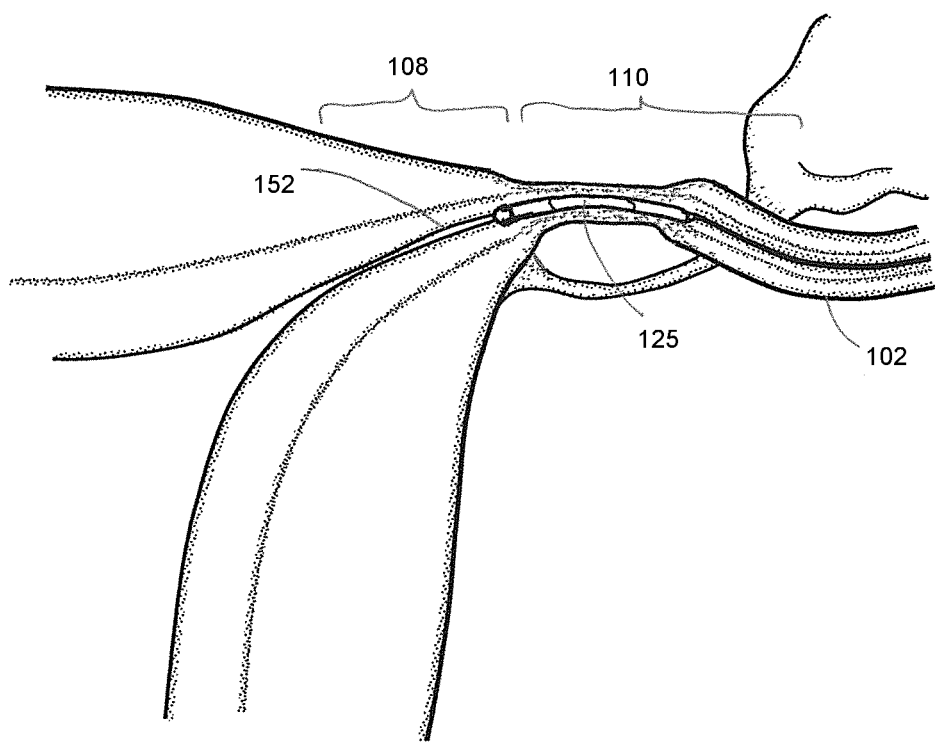
FIG. 1E is a view similar to that of FIG. 1D illustrating another step in the method wherein the guidewire is withdrawn from the implant and the resilient implant moves to its non-tensioned configuration to flatten the fallopian tube.

FIG. 1E shows the implant 125 in the fallopian tube after being de-coupled from the catheter and the catheter is withdrawn from the fallopian tube while the implant 125 remains at the site. As will be described below, the implant when released from the catheter moves from a first more linear shape to a second non-linear shape that is adapted to flatten the fallopian tube to thereby approximate walls of the fallopian tube.

Now turning to FIGS. 2A-2B, the implant 125 can be described in more detail. The implant body 144 can be fabricated of a polymeric material that is flexible or the polymer can be more rigid and formed as a slotted tube as is known in the art to provide flexibility. In one variation, the implant can have a diameter ranging between 1 mm to 3 mm with a length ranging between 1 cm to 3 cm. In the variation shown in FIGS. 2A-2B, the implant has a passageway 145 to allow it to be advanced over guidewire 148. The guidewire 148 can have a highly flexible tip portion 160 adapted for negotiating through a tortuous path of a fallopian tube and a stiffer portion 162 proximal to the highly flexible portion that can function to straighten the fallopian tube and also maintain the implant in a suitable linear shape as in FIG. 2B. In the variation of FIGS. 2A-2B, the implant 125 can be maintained in a tensioned shape by guidewire 148 as shown in FIG. 2A which allows for introduction into the fallopian as shown in FIGS. 1C and 1D.

FIGS. 2A-2B further illustrate an energy delivery component of the system wherein the implant 125 carries opposing polarity bi-polar electrodes 165A and 165B that are operatively coupled to RF source 170 and controller 175. The spaced apart electrodes 165A and 165B are shown in FIGS. 2A-2B in a helical configuration over the length of the implant but it should be appreciated that such electrodes can have any form or pattern, including circular, linear, dotted, fragmented or concentric in an outer implant surface an inner passageway of the implant. In operation, the RF source can be actuated at a suitable power level for about 5 seconds to 1 minute to ablate tissue in the fallopian tube lumen. In one variation, the mucosal layer is ablated over the length of the implant that can be from 1 cm to 3 cm. In this variation, the duty cycle of RF energy delivery can further ablate the underlying circular, longitudinal and spiral muscle layers, which can be a depth of about 0.25 mm to 1 mm. The ablation of the muscle fibers over an elongated segment then will prevent peristalsis and antiperistalsis and thereby assist in preventing displacement of the implant 125 and blood and/or coagulum. The ablation step typically would be performed with the implant in its tensioned shape with the guidewire straightening the implant. In another variation of the method, the ablation step could be performed following withdrawal of the guidewire 148 with the implant 125 in it non-tensioned configuration. The implant 125 can be a resilient polymer that is pre-formed in a curved or sinuous shape, wherein the inherent spring-ability of the implant body will urge it toward its non-tensioned curved shape. In another variation, the implant's resiliency to urge its shape toward its curved shape of FIG. 2B also be assisted by a metal spring element embedded in the implant body 144. The implant can have any curved shape that can include 1-10 or more curves or a similar number of angled portions with living hinges. In one variation the curved or angled portions are configured to provide a flat or planar shape when the implant is in its non-tensioned position to flatten the fallopian tube 102 to thereby approximate the walls of the tube.

FIGS. 2A-2B further illustrate a mechanism carried by the catheter and implant 125 that can be actuated to cause trauma at the site. In one variation shown in FIG. 2A, it can be seen that a thin flexible blade 180, for example, made of ribbon stainless steel as used in razor blade, can be moved axially in slot 182 that extends through the catheter and implant 125 to exit an open slot termination 185 to pierce and cut tissue. The blade 180 can be extended from open termination 185 an extension distance of 1 mm to 5 mm, and usually from 1 mm to 2 mm. In any event, the depth of penetration of blade 180 into tissue is greater than the depth of the ablation to ensure trauma that produces a wound healing response through any ablated layer. In use, with reference to the method steps of FIGS. 1D and 1E, the catheter and implant 125 can be rotated in either direction, and at various degrees of rotation, the blade 180 can be extended and retracted to cut tissue and cause bleeding. In use, the blade 180 can be extended following the ablation step with the implant 125 in either its tensioned configuration (FIGS. 1D and 2A) or non-tensioned configuration (FIGS. 1E and 2B).

Figure 3:
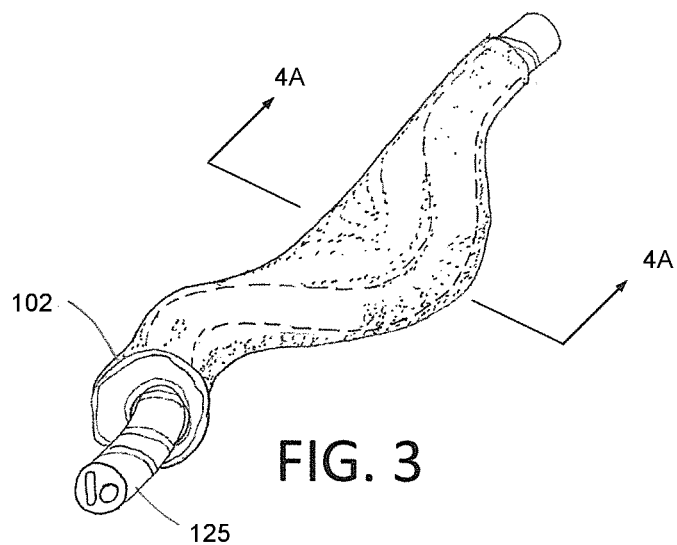
FIG. 3 is a graphic representation of the fallopian tube with the tube walls approximated which corresponds to the method step shown in FIG. 1E.

In another aspect of the method step shown in FIGS. 1D and 1E, a negative pressure source 190 can be actuated contemporaneous with or subsequent to the cutting step to draw blood from the cut tissue into the site. As can be understood from FIGS. 2A-2B, the negative pressure source 190 can be actuated manually or by controller 175 in unison with the ablative energy, or automatically timed to follow the actuation of ablative energy. The negative pressure or suction can communicate with the targeted site through the guidewire passageway 148 in the catheter and implant 125, and/or the slot 182 for blade 180 that extends through the catheter and implant. In FIGS. 2A-2B, the guidewire passageway 148 communicates with the negative pressure source 190 to thereby apply suction forces through a plurality of ports 192 in the implant 125. In one variation, the suction forces are pulsed to sustain bleeding into the site. FIGS. 3-4B show that the blade 180 along with the guidewire 148 can be withdrawn from the implant 125.

In one variation, the implant 125 is releasably carried by the catheter within the retractable sheath 158. Thus, after the sheath is withdrawn as illustrated in FIG. 1D, the implant 125 is free from the catheter shaft but still stabilized in place by the guidewire 148. In other variations, variation, the implant can be released from the catheter shaft by means known in the art, such as (i) a tear-away connection that is broken by retraction of the guidewire 148 or blade 180, (ii) a mechanical mechanism such as a latching collar; (iii) a meltable polymer connection that can be melted by RF or resistive heating; (iv) a frangible connector actuated and broken by a heated NiTi element; or (v) an electrolytic detaching mechanism as known in the art of detachable embolic coils.

Figure 4A:
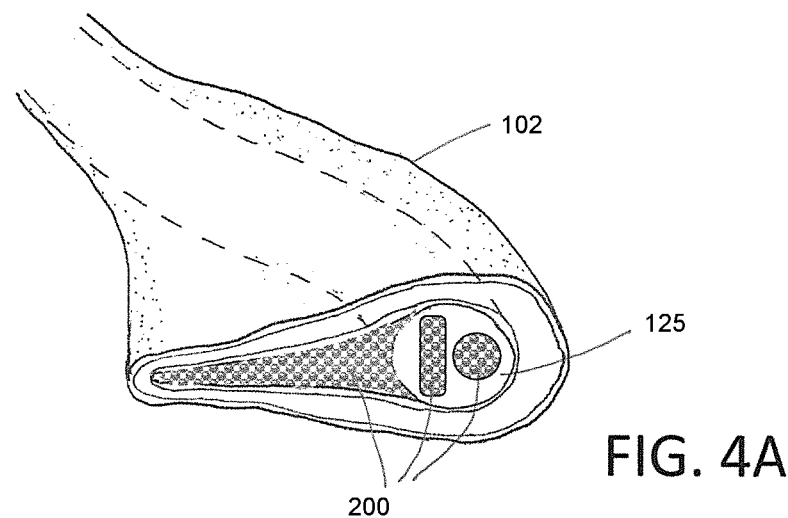
FIG. 4A is a sectional view of the fallopian tube of FIG. 3 taken along line 4A-4A which again corresponds to the method step shown in FIG. 1E wherein blood accumulates and is trapped in the fallopian tube.
Figure 4B:
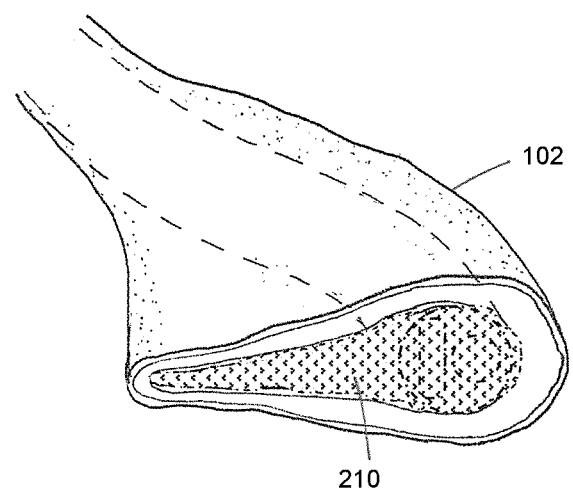
FIG. 4B is a sectional similar to that of FIG. 4A after the passage of time wherein an adhesion has formed across the lumen of the fallopian tube and further depicting the bioabsorption of the implant body.

Now turning to FIGS. 3-4B, it can be seen how the implant 125 is adapted to trap blood 200 and coagulum in the site. In FIG. 3, the guidewire has been withdrawn and the implant 125 is urged toward its non-tensioned shape to flatten the fallopian tube 102 wherein the approximated walls of the fallopian tube 102 will allow for more rapid adhesion formation between the opposing walls as shown in FIG. 4A.

FIG. 3 illustrates the implant 125 in a portion of the fallopian tube in its second non-linear shape approximating the walls of the fallopian tube 102. FIGS. 4A and 4B depict a portion of the fallopian tube segment following approximation of the walls with the pooling of blood and resulting coagulum in the targeted site, followed by adhesion formation in the site and bio-absorption of the body of the implant 125.

FIG. 4A illustrates blood 200 pooling in the flattened segment of the fallopian tube 102. The blood also migrates into the guidewire passageway 148 through ports 192 and into the blade slot 182 through open termination 185.

Of particular interest, it can be understood from FIG. 3 that the curved shape of implant 125 will help lock it in place in the fallopian tube 102 to resist any peristaltic forces that might otherwise dislodge the implant. Also of particular interest, the curve or curves of the implant body as shown in FIG. 3 are adapted to function as a dam to prevent the blood and subsequent coagulum from being displaced.

FIG. 4B illustrates the fallopian tube 102 being occluded with adhesion 210 which can form rapidly in a few days as the trapped blood/coagulum (FIG. 4A) functions as an optimal scaffold for fibrosis across and between the walls of the fallopian tube 102. FIGS. 1G-IH also show the flattening of the fallopian tube 102 which allows a more rapid formation of the adhesion 110 due to the reduced thickness dimension between the approximated walls of the fallopian tube 102.

FIG. 4B also is a graphic representation of one variation of the device and method wherein the implant 125 is bio-absorbable and FIG. 4b illustrates that the implant 125 has been resorbed and replaced with the adhesion 110.

Figure 5:
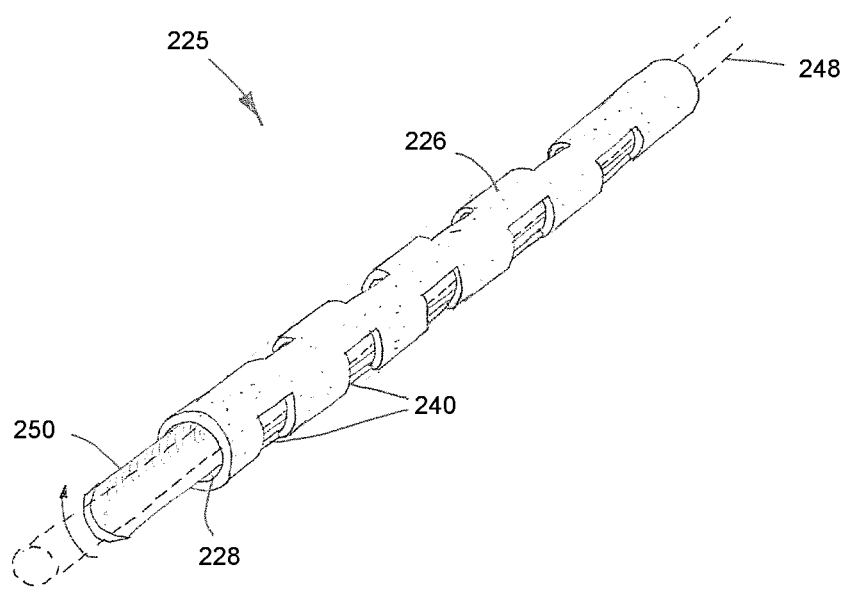
FIG. 5 is a perspective view of another variation of occluding device or implant that includes the functionality of the system and implant of FIGS. 1A-4B.

FIG. 5 illustrates another variation of implant 225 that can be used to occlude a fallopian tube using, in general, the same methods as described in FIGS. 1A-4B. The body 226 of implant 225 can comprise a slotted polymer tube having interior lumen 228 in which the slots 240 can have selected dimensions to allow a rigid polymer tube to be flexible to follow a guidewire 248 within a tortuous path. The slots can be formed to provide flexibility in 360° as is known in the art. In this respect, the polymer sleeve can comprise a bio-absorbable or bio-degradable material that is substantially rigid but made flexible by the slots 240.

Still referring to FIG. 5, the ablation functionality of the implant can again be provided by an RF source and spaced apart opposing polarity electrodes can be printed on the surface of the implant body 226. In another variation, the surface of the implant body 226 can have electro-less plating of gold or another conductive metal to provide a first electrode and the guidewire 248 can comprise a second opposing polarity electrode.

Still referring to FIG. 5, the mechanism to cause trauma associated with the implant 225 comprises a cutting element or blade 250 that extends through lumen 228 and can be actuated from the handle of the catheter and can be manually operated or motor driven. The blade 250 can be a rotatable thin linear member of a ribbon stainless steel as shown in FIG. 5, but additional variations also include a helical sharp edged element or an abrasive wire that can be moved rotational, axially or in both rotational and axial directions. An additional advantage of the variation of FIG. 5 is that the negative pressure source 190 can suction tissue into lumen 228 and the tissue can be cut and captured in the lumen 228. The cutting depth is sufficient to cut through the ablated tissue layer. The implant 225 can be moved slightly both axially and rotationally while actuating the blade to resect the entire surface layers of the fallopian tube lumen 152. As a result, trauma is caused and further, the approximated walls or the fallopian tube 102 will be raw tissue, instead of ablated layers with cuts therein as shown in the embodiment in FIGS. 1A-4B. It is believed that adhesions will form more quickly with the exposed cut tissue interfacing the coagulum in the targeted site (cf. FIGS. 3-4B).

Still referring to FIG. 5, the implant 225 can flatten the fallopian tube by providing a pull wire in the side of the sleeve to cause a curve in the implant (not shown). In another variation, a heat shrink polymer can be provided on one side of the implant that can be heated to deform the implant. Thus, the implant 225 of FIG. 5 can provide all the functions as described in the previous embodiment, including: flexibility to follow a tortuous path, an RF electrode arrangement to ablate tissue, a cutting mechanism to cause bleeding in a targeted site, means to flatten the fallopian tube and means to trap the coagulum in the targeted site.

Figures 6A, 6B:
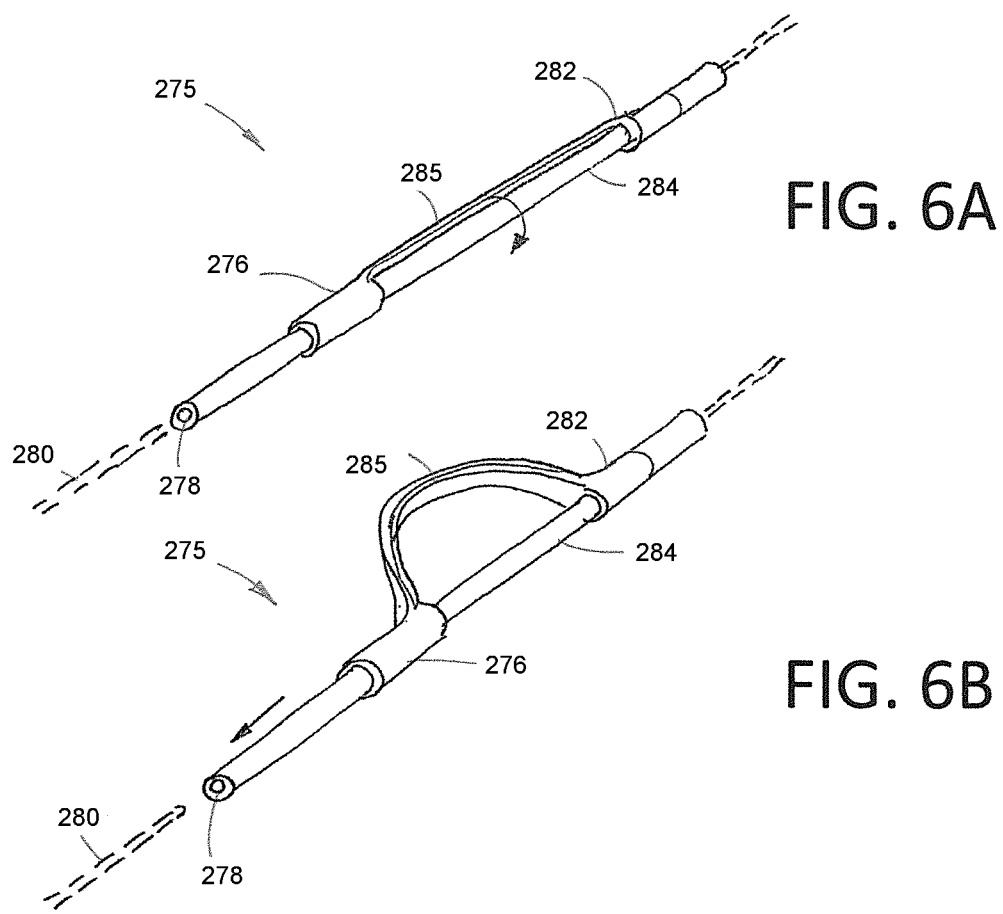
FIG. 6A is a perspective view of another variation of occluding device or implant in a collapsed or non-extended position.
FIG. 6B is a view of the implant of FIG. 6A in an extended position.

FIGS. 6A-6B illustrate another variation of implant 275 for occluding a fallopian tube that can function to perform the methods as described previously. The body 276 of implant 275 again can comprise polymers with a guidewire lumen 278 to accommodate guidewire 280. The implant has first and second (outer and inner) elements 282 and 284 that can be actuated to flatten the fallopian tube lumen. The outer element 282 has a flexible medial section that carries an abrasive edge 285 for example of diamond powder. Thus, the outer element 282 can be rotated to abrade and cut tissue to cause trauma when in a collapsed or partly collapsed position. Further, the inner and outer elements 282 and 284 can be patterned with surface electrodes to perform the ablation step. To actuate the implant to an expanded shape as in FIG. 6A, the inner element 284 can be pulled proximally to bend the outer element 284 which can be locked in place by a ratchet mechanism, heat actuated melt adhesion of the elements or any suitable mechanical locking mechanism. Thus, the implant 275 of FIGS. 6A-6B can again provide the key functions of previous variations, including: flexibility to follow a tortuous path, an RF electrode arrangement to ablate tissue, a cutting mechanism to cause trauma in a targeted site, means to flatten the fallopian tube and means to trap the coagulum in the targeted site.

FIGS. 7A-7B depict another variation of implant 325 for use in occluding a fallopian tube that again can function to perform the methods described above. The body 326 of implant 325 has first and second, or respectively, outer and inner polymer sleeve elements 332 and 334 that can be actuated to expand leg elements 335 laterally to flatten the fallopian tube lumen. It can be seen that the outer element has a plurality of slots 340 and the inner element 334 has living-hinged leg elements 335 that can lay flat in the slots 340 in the insertion configuration of FIG. 7A. The inner sleeve 334 can be moved axially relative to outer sleeve 332 over guidewire 342 as shown in FIG. 7B to cause the leg elements 335 to be flexed outwardly. The extended leg elements 335 then will trap blood and coagulum in the site, with the mechanism to cause bleeding described below.

In order to perform the step to cause trauma in the targeted site in a fallopian tube, the outer sleeve element 332 has a surface 345 covered at least in part with abrasive particles, for example diamond particles or powder bonded to the surface 345. Thus, the outer element 332 can be rotated to abrade and cut tissue to cause bleeding (or trauma as described herein) when the implant 325 is in the non-expanded position of FIG. 7A. The implant 325 also allows for negative pressure to be applied to the site through the outer sleeve lumen 350 that accommodates the inner sleeve 334. In order to provide the ablation step, the outer surface 345 also can comprise a first polarity electrode with the guidewire 342 comprising the second polarity electrode.

To actuate the implant 325 to an extended or expanded shape of in FIG. 7B, the inner element 334 is pulled proximally to outwardly flex the leg elements 335 which can be locked in place by a ratchet mechanism, heat actuated melt adhesion of the elements or any suitable mechanical locking mechanism. Thus, the implant 325 of FIGS. 7A-7B can again provide the functionality of previous variations, including: flexibility to follow a tortuous path, an RF electrode arrangement to ablate tissue, an abrasive mechanism to cause trauma in a targeted site, means to flatten the fallopian tube and means to trap the coagulum in the targeted site.

Figure 8:
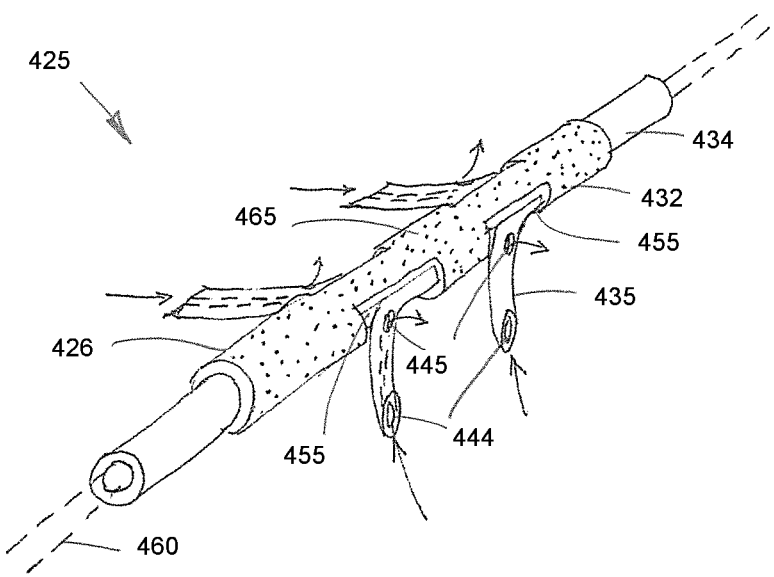
FIG. 8 is a perspective view of another variation of occluding device or implant in an actuated position.

FIG. 8 illustrates a portion of another variation of implant 425 for occluding a fallopian tube that functions to perform methods described previously and is similar to the implant 325 of FIGS. 7A-7B. In FIG. 8, the body 426 of implant 425 has outer and inner polymer sleeve elements 432 and 434 that are actuated to extend leg elements 435 outwardly. In this variation, the leg elements 435 are hollow and needle-like to penetrate tissue and allow bleeding to flow back to the site through ports 444 and 445. In other respects, the implant 425 is similar to that of FIGS. 7A-7B with the leg elements 435 being collapsible into a plurality of slots 455. The inner sleeve 434 is moved axially relative to outer sleeve 432 over guidewire 460 and the extended legs 435 then will trap blood and coagulum in the site. The mechanism to cause bleeding is described in the previous embodiment. The outer sleeve element 432 has a surface 465 covered at least in part with abrasive diamond particles bonded to the surface 465. Thus, the outer element 432 can be rotated to abrade and cut tissue to cause bleeding when the implant 425 is in the non-expanded position as in FIG. 8. The outer surface 465 can comprise a first polarity electrode as described previously.

FIGS. 9A-9C illustrate another variation of implant 515 for a fallopian tube that comprises a flexible polymer with multiple flex elements 518 that can flex outwardly to flatten a fallopian tube 102. The flex elements 518 can be resilient and flex outward as in FIG. 9B after retraction of a retaining sheath (cf. FIGS. 1D, 1E and 2B). Alternatively, the flex elements 518 can be flexed by the pull of an inner sleeve in guidewire lumen 520 as shown in the embodiment of FIGS. 6A-6B. The implant 515 can have an abrasive surface 522 for causing trauma as described previously as well as surface electrodes as described in earlier embodiments.

FIGS. 10A-10B illustrate another variation of implant 525 for occluding a fallopian tube that comprises a polymer with hinged elements 528 that can flex outwardly to flatten a fallopian tube. This embodiment includes barbs 540 for penetrating and gripping tissue. It should be appreciated that all of the previous variations can include barb features for engaging the walls of the fallopian tube. In one variation, an implant can have barbs that point in both the proximal and distal directions to assist in resisting dislodgement when subjected to both peristalsis and antiperistalsis. The implant 525 can have an abrasive surface 522 for causing trauma and surface electrodes as described in earlier embodiments.

Figure 11A:
FIG. 11A is a perspective view of another variation of the implant in an insertion configuration.
Figure 11B:
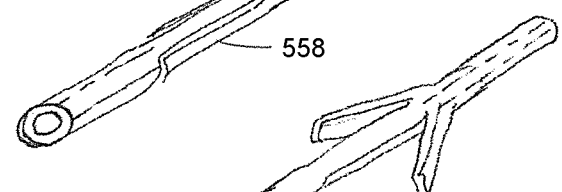
FIG. 11B is a view of the implant of FIG. 11A is a deployed configuration.
Figure 12A:
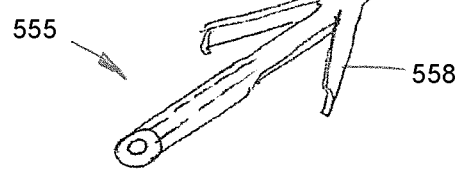
FIG. 12A is a perspective view of another variation of the implant in an insertion configuration.
Figure 12B:
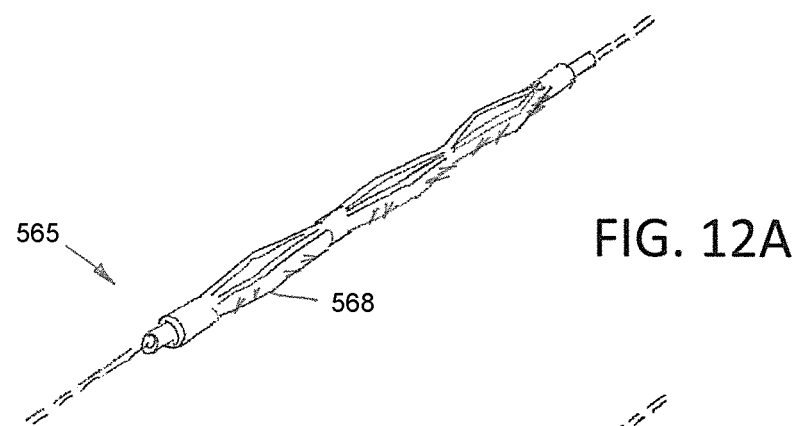
FIG. 12B is a view of the implant of FIG. 12A is a deployed configuration.

FIGS. 11A-11B illustrate another variation of implant 555 for occluding a fallopian tube that has resilient polymer barb elements 558 that flex outwardly to grip and flatten a fallopian tube. FIGS. 12A-12B depict another variation of implant 565 that has resilient flex elements 568 that flex outwardly and have barbs 570 facing both proximal and distal directions to engage and flatten a fallopian tube. The variations of FIGS. 11A, 11B, 12A and 12B can include a retractable sheath as described previously as well as surface electrodes as described above.

In some embodiments above, the polymer implants are of a bio-absorble material. Such materials are well known in the art and can be described as bio-resorbable, absorbable bio-erodible and can be assimilated by the body at predictable rates. Bio-resorbable or bio-degradable polymers include polylactic acid (PLA) polyglycolic acid (PGA), polydioxanone (PDS), polyhydroxybutyrate (PHB), polyhydroxyvalerate (PHV), polycaprolactone, polycyanocrylates, or polyphosphazenes. As used herein, the term bio-resorbable includes a suitable bio-compatible material, mixture of materials or partial components of materials being degraded into other generally non-toxic materials by an agent present in biological tissue, for example by being biodegradable or being removed by cellular activity, by bulk or surface degradation, or a combination of one or more of bio-degradable, bio-erodable, or bio-resorbable materials.

A number of embodiments of the invention have been described. Nevertheless, it will be understood that various modifications may be made without departing from the spirit and scope of the invention. Combination of the aspects of the variations discussed above as well combinations of the variations themselves are within the scope of this disclosure.

What is claimed is:

1. A method for occluding a fallopian tube, comprising:
    advancing a delivery catheter having an implant to position the implant in a site in the fallopian tube;
    activating an energy source to deliver energy to the implant to ablate fallopian tube tissue at the site;
    producing a wound at the site in the fallopian tube to cause a wound healing response at the site that produces an adhesion of walls of the fallopian tube;
    decoupling the implant from the delivery catheter; and withdrawing the delivery catheter from the fallopian tube while the implant remains at the site.

2. The method of claim 1, further comprising approximating opposing walls of the fallopian tube with the implant to assist in creating the adhesion.

3. The method of claim 2, wherein withdrawing the delivery catheter from the site causes the implant to change shape to flatten the fallopian tube to thereby approximate opposing fallopian tube walls.

4. The method of claim 1, wherein advancing the delivery catheter includes advancing the delivery catheter over a guidewire.

5. The method of claim 1, wherein advancing the delivery catheter includes advancing the delivery catheter and implant over a guidewire.

6. The method of claim 1, wherein the site is an intramural or isthmus region of the fallopian tube.

7. The method of claim 1, wherein advancing the delivery catheter to position the implant in the site further comprises deforming a shape of the implant to flatten the fallopian tube to thereby approximate opposing fallopian tube walls.

\* \* \* \* \*